United States Patent [19]

Smits et al.

[11] 4,074,721
[45] Feb. 21, 1978

[54] BREAST PADS

[75] Inventors: Donald M. Smits; Patrick J. Daley, both of Green Bay, Wis.; Arnold J. Akerley, Westboro, Mass.

[73] Assignee: The Kendall Company, Walpole, Mass.

[21] Appl. No.: 754,384

[22] Filed: Dec. 27, 1976

[51] Int. Cl.² ............................................. A41C 3/00
[52] U.S. Cl. ................................................. 128/461
[58] Field of Search ............... 128/461, 484, 289, 505, 128/464

[56] References Cited

U.S. PATENT DOCUMENTS

| 2,047,522 | 7/1936 | Schnaittacher | 128/461 |
| 2,748,771 | 6/1956 | Richards | 128/461 |
| 2,891,544 | 6/1959 | London | 128/461 |
| 3,280,818 | 10/1966 | Pankey et al. | 128/505 |

Primary Examiner—Doris L. Troutman

[57] ABSTRACT

A pad for absorbing lacteal fluid is constructed comprising an absorbent central portion, a moisture-impermeable outer portion, and a fluid-transmitting body-contacting portion. Between the body-contacting portion and the absorbent central portion there is positioned a layer of material which has a higher degree of capillary transfer of lacteal fluid than said body-contacting portion, whereby capillary spread of fluid in said body-contacting portion is minimized.

3 Claims, 7 Drawing Figures

BREAST PADS

This invention relates to breast pads to be worn by nursing mothers. More particularly it relates to breast pads designed to minimize irritation caused by the retention of lacteal fluid on the body-contacting portion of the pad.

Breast pads are commonly prepared by sandwiching a relatively thick layer of absorbent material between a thin outer layer of material, usually non-absorbent, and a thin absorbent inner or body-contacting layer. Various combinations of gauze, cellulose wadding, nonwoven fabrics, cellular sponge material, plastic film, and the like, have been utilized as structural elements, with varying degrees of effectiveness.

Prior art devices, however, generally suffer from one of two disadvantages. Either the body-contacting face of the pad becomes saturated with lacteal fluid, leading to irritation of the breast, or else efforts to circumvent this irritation have been involved structurally and expensive to manufacture.

It is an object of this invention to produce a breast pad with a body-contacting layer which will remain relatively dry and comfortable in use, by a simple and economical process.

The invention will be better understood by reference to the following description and drawings, in which.

Figure 5:
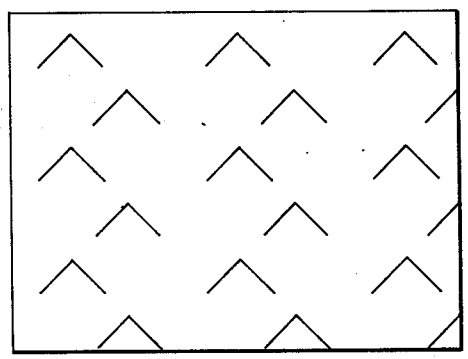
Figure 7:
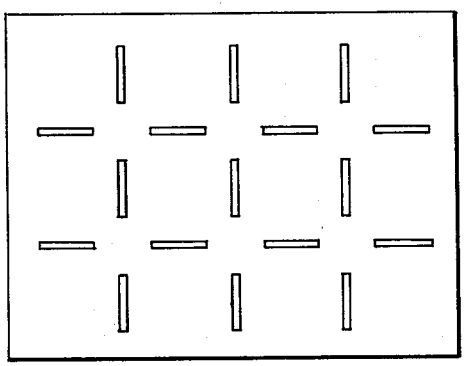
Figure 6:
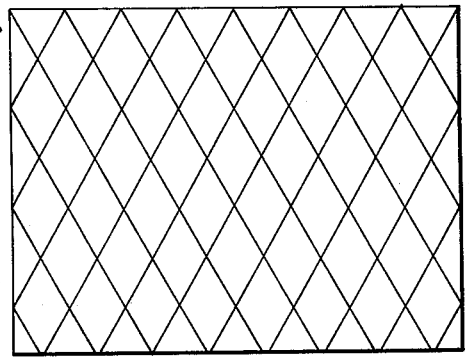

FIGS. 5, 6, and 7 are representation of alternative body-contacting layers suitable for use in this invention.

Figure 1:
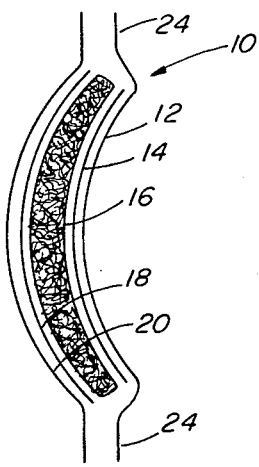
FIG. 1 is a perspective view of the layers of material employed in the manufacture of the pad.

Referring to FIG. 1, the breast pad 10 comprises a body-contacting layer of nonwoven fabric 12, more explicitly described herein below; two layers of cellulose wadding, 14 and 18, enclosing the principal absorbent layer 16; and a moisture-impervious outer layer 20. The body-contacting layer 12 and the outer layer 20 are sealed together into a peripheral flange 24 extending around the circumference of the circular pad, and encapsulating therein the absorbent layer 16 and the wadding layers 14 and 18.

The principal absorbent layer 16 is preferably of very short absorbent cellulose fibers, such as bleached and macerated wood pulp, or fluff. Such an array of fibers has a very high absorbent capacity, up to 25 times its weight in water, and at the same time forms a soft and conformable cushion, allowing the circular pad to be die-shaped into the form of a shallow cup. It is, however, lacking in integrity and tensile strength. Therefore, one function of the layers of cellulose wadding, 14 and 18, is to secure the fluff layer 16 against disruption or displacement in use. For this purpose, in constructing the three absorbent inner layers of the pad, a substantially uniform layer of fluff is blown onto a sheet of wadding, a second sheet of wadding is superimposed onto the top of the fluff layer, and the three-ply assembly is subjected to sufficient pressure to bring the fluff and the wadding into intimate contact. The assembly of wadding and fluff is then die-cut into circles of convenient size, as for example 4 to 5 inches in diameter.

Figure 2:
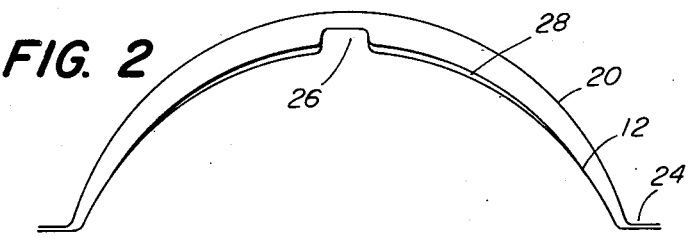
FIG. 2 is a side elevation of a typical pad of this invention, in cross-section.

If desired, the die may be fashioned so that simultaneously with the cutting it imparts to the assembly a compressed central depression from which radiates a series of compressed radial lines or channels, 26 and 28 respectively in FIG. 2.

The central depression is circular in shape, designed to accommodate the nipple of a nursing breast, adding to comfort in use. The radial compressed channels 28 form a series of zones of high capillarity in the absorbent fluff layer whereby lacteal fluid is transported away from the central zone of the pad, thus minimizing saturation in the central zone.

The fluid-impermeable outer layer 20 is preferably a layer of thin, conformable plastic film such as polyethylene, polypropylene, or the like and for convenience in handling it may be laminated to a thin sheet of tissue or cellulose wadding, not shown. Such film-tissue laminates are commercially available, and the adhesive attachment of the tissue to the film may be made discontinuous, in the form of intermittent spots or criss-crossing lines of adhesive. Where such a tissue-film laminate is employed, as in the preferred embodiment of this invention, the tissue face is positioned on the outside of the pad, thus minimizing the danger of slippage or maladjustment of the pad, since the tissue surface has more positive frictional engagement with the clothing than does the film surface.

The body-contacting layer 12 is a soft, comfortable layer of non-woven fabric of high air and liquid permeability but of low capillarity so far as liquid spread is concerned. Preferably this nonwoven fabric comprises absorbent rayon or cotton fibers, bonded for wet strength by a soft, flexible polymeric binder applied in a discontinuous pattern over a portion only of the surface of the fibrous web.

Capillary spread of liquid in a nonwoven fabric tends to be predominant in the direction of the principal orientation of the fibers, since parallel fibers serve as a set of fine capillaries or wicks, enhancing liquid transmission. In a fabric made from carded fibers, the fibers are highly oriented in the machine or long direction. In order to minimize the tendency of absorbed liquid to spread along the length of the fabric, in the principal direction of fiber orientation, the polymeric binder may be applied in a set of spaced-apart wavy lines, running more or less continuously across the width of the nonwoven fabric, in known manner. Alternative bonding patterns, serving similar functions, are shown in FIGS. 5, 6 and 7, and it will be obvious to one skilled in the art that numerous patterns of discontinuous bonding may be employed, depending on the predominant fiber orientation in the nonwoven fabric.

Figure 4:
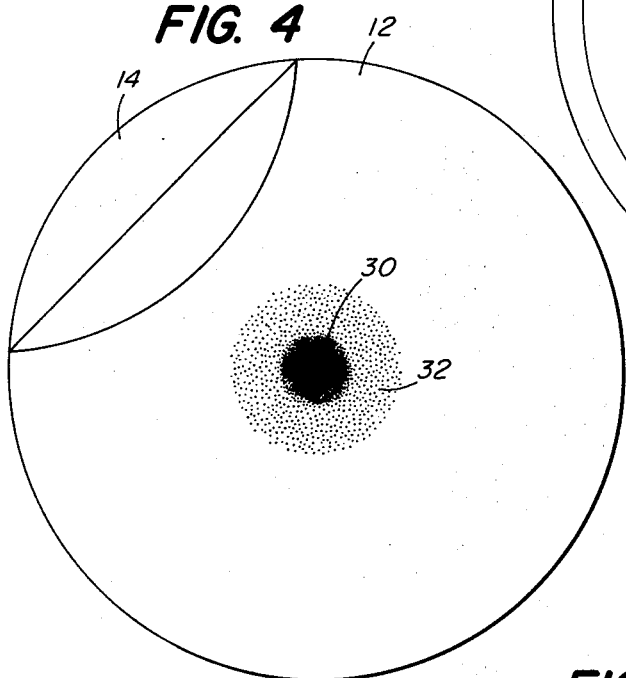
FIG. 4 is a representation, partly folded back, of the interaction of the body-contacting layer and the adjacent transmission layer of the pad.

Such a discontinuous binder pattern does not inhibit the spread of applied liquid, but does impede it to such an extent that the fluid tends to transfer itself to the underlying layer of cellulose wadding or tissue, 14, with which the body-contacting layer 12 is in contact. The tissue layer 14 contains no binder or other impediment to capillary spread of liquid so that liquid applied to the surface of a breast pad of this invention develops a moisture pattern represented by FIG. 4, where the nonwoven fabric layer 12, partly peeled back, is marked by a relatively small spot of moisture 30, while the underlying layer of tissue 14 is marked by a substantially larger area of moisture 32. It is characteristic of the breast pads of this invention that the moistened area developed in the tissue layer is about four times the moistened area in the body-contacting nonwoven fabric layer. As more liquid is applied to the pad, this ratio is maintained, with more and more liquid being passed through the tissue layer 14 to be taken up by the main body of absorbent fluff 16.

By thus impeding the spread of liquid in the body-contacting layer 12, and encouraging liquid transfer to the absorbent center of the pad, the body-contacting surface of the pad remains relatively dry in comparison with prior art devices. Irritation and maceration of breast tissue are thus minimized.

Figure 3:
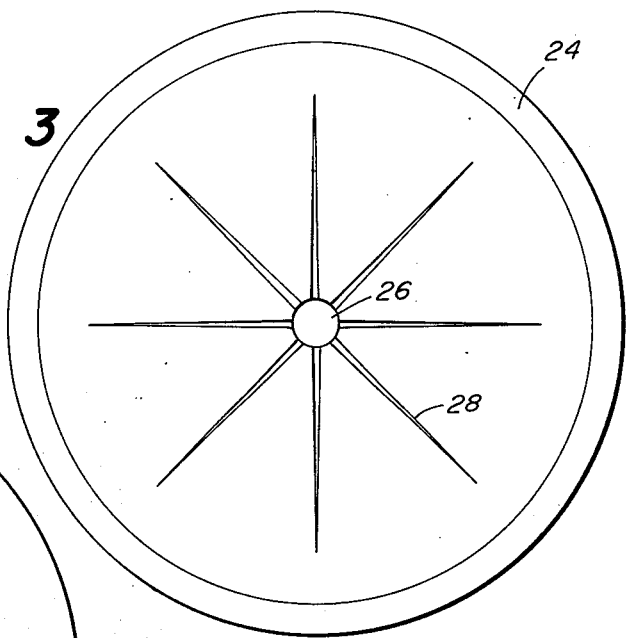
FIG. 3 is a front elevation of the pad of FIG. 2.

In producing breast pads according to this invention, the circular die-cut pieces of absorbent fluff, faced with the wadding layers 14 and 18, are superimposed in spaced-apart relation upon a sheet of suitable nonwoven fabric 12, previously described, and a sheet of film-wadding laminate 20 is brought into contact with the upper surface of the assembly, with the tissue face of the laminate uppermost. If the film is of a thermoplastic nature, heated circular dies may be used to bring the nonwoven fabric layer 12 and the film-tissue laminate layer 20 into intimate sealed contact, forming the peripheral flange 24 shown in FIGS. 2 and 3. Alternatively, the film-tissue laminate may be coated with adhesive prior to being brought into contact with the assembly, whereby a simple pressure and die-cut operation forms the flange. Simultaneously with this sealing and cutting operation, the circular pads are formed into the shape of a shallow cup.

It will be appreciated that the foregoing description is illustrative only, and that the pad may be varied in details without departing from the spirit of the invention.

Having thus described our invention, we claim:

1. A cup-shaped breast pad having a first layer forming a body-contacting surface of nonwoven fabric characterized by rapid liquid transmission but low capillary spread of liquid;
   a second layer of smaller diameter than said first layer, said second layer consisting of absorbent cellulose wadding characterized by a higher degree of capillary transfer of liquid than said first layer and being centrally disposed on said first layer and coextensive therewith;
   a third layer of absorbent cellulose fluff coextensive with said second layer;
   a fourth layer of absorbent cellulose wadding coextensive with said third layer;
   and a fifth layer of liquid-impermeable material coextensive with said first layer;
   said first layer and said fifth layer being adhesively united to each other around substantially the entire periphery of both layers.

2. The pad according to claim 1 in which said first layer of nonwoven fabric is bonded by a set of discrete and spaced-apart areas of polymeric binding material, said areas impeding the capillary spread of liquid applied to said fabric.

3. The pad according to claim 1 wherein the absorbent layers of the pad are characterized by a centrally located depression and a series of radially extending channels of enhanced capillarity.

* * * * *